(12) United States Patent
Yanai et al.

(10) Patent No.: US 6,211,145 B1
(45) Date of Patent: Apr. 3, 2001

(54) BICYCLIC DEPSIPEPTIDES

(75) Inventors: Makoto Yanai; Masashi Suzuki; Norio Oshida; Koji Kawamura; Shigeru Hiramoto; Orie Yasuda; Nobuhiro Kinoshita; Akiko Shingai; Masako Takasu, all of Saitama-ken (JP)

(73) Assignee: Nisshin Flour Milling Co., Ltd., Tokyo (JP)

( * ) Notice: Subject to any disclaimer, the term of this patent is extended or adjusted under 35 U.S.C. 154(b) by 0 days.

(21) Appl. No.: 09/212,481

(22) Filed: Dec. 16, 1998

(30) Foreign Application Priority Data

Dec. 25, 1997 (JP) .................................................. 9-357749

(51) Int. Cl.[7] .............................. A61K 38/08; C07K 7/06
(52) U.S. Cl. .................................. 514/10; 514/9; 514/16; 530/317; 530/323; 530/329
(58) Field of Search .................. 514/10, 9, 16; 530/323, 317, 329

(56) References Cited

U.S. PATENT DOCUMENTS 5,801,143   9/1998   Hiramoto et al. ........................ 514/9

FOREIGN PATENT DOCUMENTS 0 761 682   3/1997   (EP) .
WO97/49724   12/1997   (WO) .

OTHER PUBLICATIONS

Michael J. Ignatius, et al., "Expression of Apolipoprotein E During Nerve Degeneration and Regeneration," Proc. Natl. Acad. Sci. USA, vol. 83, (Feb. 1986), pp. 1125–1129.
Nobuhiro Yamada, et al., "Increased Clearance of Plasma Cholesterol After Injection of Apolipoprotein E Into Watanabe Heritable Hyperlipidemic Rabbits," Proc. Natl. Acad. Sci. USA, vol. 86, (Jan. 1989), pp. 665–669.

Hitoshi Shimano, et al., "Plasma Lipoprotein Metabolism in Transgenic Mice Overexpressing Apolipoprotein E," Journal of Clinical Investigation, vol. 90, (Nov. 1992), pp. 2084–2091.

*Primary Examiner*—Christopher S. F. Low
*Assistant Examiner*—Abdel A. Mohamed
(74) *Attorney, Agent, or Firm*—Oblon, Spivak, McClelland, Maier & Neustadt, P.C.

(57) ABSTRACT

The present invention provides a bicyclic depsipeptide having the formula (1)

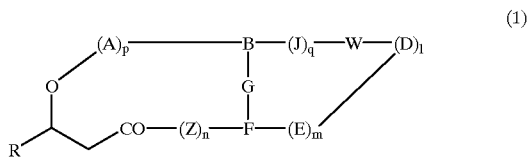

wherein:

R is a straight or branched alkyl group of 5–20 carbon atoms or a straight or branched alkoxymethyl group of 5–15 carbon atoms; A, D, E and J independently are a residue of an amino acid selected from the group of alanine, valine, leucine, etc.; B and F are the same or different and a residue of an amino acid selected from the group consisting of cysteine, aspartic acid, glutamic acid, lysine, hydroxylysine and serine; G is a disulfide bond, an amido bond or an ester bond; W is a residue of an amino acid selected from the group consisting of aspartic acid and glutamic acid; Z is a residue of an amino acid selected from the group consisting of aspartic acid, asparagine, glutamic acid and glutamine; l, m, n, p and q independently are 0 or 1; or a pharmacologically acceptable salt thereof.

9 Claims, No Drawings

BICYCLIC DEPSIPEPTIDES

BACKGROUND OF THE INVENTION

1. Field of the Invention

This invention relates to a bicyclic depsipeptide and a pharmaceutical composition containing the same as an active ingredient. The bicyclic depsipeptides of the invention have a promoting activity on the production of apolipoprotein E which has a repairing action on neurologic damages so that the bicyclic depsipeptides of the invention are useful as the therapeutic agents for neurologic damages, especially as an antidementia agent, and also as a therapeutic agent for hyperlipemia.

2. Description of the Prior Art

As a therapeutic agent for senile dementia, there have been mainly applied activators of cerebral circulation and metabolism, but these drugs have no improving effect on disintegration of the central nervous system which is believed to cause senile dementia. Consequently, they do not display any improving effect on dysmnesia or acalculia which is said to be the main symptom of dementia. On the other hand, it has been reported that apolipoprotein E may be generated at a high level at the damaged sites of nervous systems which are being repaired (For example, refer to M. J. Igunatius et al., Proc. Natl. Acad. Sci. U.S.A., 83, 1125 (1986)), which suggests that apolipoprotein E will play an important role in repairing the nervous systems.

Moreover, it has recently been reported that a remarkable reduction in a plasma cholesterol level is observed when apolipoprotein E is administered intravenously to WHHL rabbit which is a model animal for human familial hypercholesterolemia homozygote (Yamada et al., Proceeding of National Academy Science USA, Vol. 86, pp. 665–669, 1989). Also, it has been reported that plasma cholesterol and plasma triglyceride can be noticeably decreased by transducing a gene for apolipoprotein E into the mouse liver and expressing apolipoprotein E in a large mass (Shimano, H. et al., Journal of Clinical Investigation, Vol. 90, pp. 2084–2091, 1992).

As is apparent from these reports, an increase in apolipoprotein E level in plasma has been regarded as extremely effective in the treatment of hyperlipemia, especially, familial hypercholesterolemia homozygote which has been hitherto considered as difficult to be treated with the prior art drugs.

DETAILED DESCRIPTION OF THE INVENTION

In view of the foregoing, there has been desired as a novel type of a therapeutic agent for senile dementia a drug which may promote the repair and growth of the nervous systems and inhibit the disintegration of the central nervous system, besides activators of cerebral circulation and metabolism.

Also, it has been desired to elucidate a drug which may increase apolipoprotein E level in plasma as a therapeutic method for hyperlipemia, especially, familial hypercholesterolemia homozygote which has been hitherto considered as difficult to be treated with the prior art drugs.

Under these circumstances, we have made our earnest studies to provide a drug for promoting the production of apolipoprotein E, and as a result, a certain bicyclic depsipeptide may possess such an activity, upon which this invention has been completed.

The present invention relates to a bicyclic depsipeptide having the formula (1)

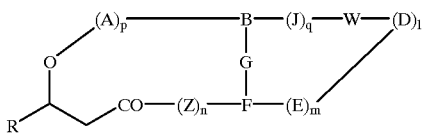

or a pharmacologically acceptable salt thereof.

In the above formula (1), R is a straight or branched alkyl group of 5–20 carbon atoms or a straight or branched alkoxymethyl group of 5–15 carbon atoms; A, D, E and J independently are a residue of an amino acid selected from the group of alanine, valine, leucine, isoleucine, serine, threonine, lysine, hydroxylysine, arginine, cysteine, methionine, phenylalanine, tyrosine, tryptophan, histidine, proline, 4-hydroxyproline, aspartic acid, glutamic acid, piperidine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)piperidylalanine, 3-(2-naphthyl)alanine, β-cyclohexylalanine, β-t-butylalanine, 9-anthracenylalanine, α-methylalanine or 2-aminobutanoic acid which is optionally substituted with an N-($C_1$–$C_4$) alkyl; B and F are the same or different and a residue of an amino acid selected from the group consisting of cysteine, aspartic acid, glutamic acid, lysine, hydroxylysine and serine; G is a disulfide bond, an amido bond or an ester bond; W is a residue of an amino acid selected from the group consisting of aspartic acid and glutamic acid; Z is a residue of an amino acid selected from the group consisting of aspartic acid, asparagine, glutamic acid and glutamine; l, m, n, p and q independently are 0 or 1; provided that G is formed by binding each other a thiol, carboxyl, hydroxyl or amino group contained in the amino acid residues B and F, a free amino, carboxyl, hydroxyl, mercapto or ω-carbamido group which possibly exists in said amino acid residue may be protected by a group commonly used in peptide chemistry as a protective group and when A, B, D, E, F, J, W and Z are a residue of lysine, hydroxylysine, glutamic acid or aspartic acid, either α- or ω-amino or carboxyl group existing in said residue may form a peptide linkage with its adjacent amino acid.

The invention specifically relates to a bicyclic depsipeptide having the formula (1) wherein A, J, D and E independently are a residue of an amino acid selected from the group of alanine, valine, leucine, isoleucine, serine, threonine, lysine, arginine, cysteine, methionine, phenylalanine, tyrosine, tryptophan, histidine, proline, aspartic acid and glutamic acid or an N-($C_1$–$C_4$) alkyl substituted amino acid residue thereof, or a pharmacologically acceptable salt thereof.

The compound of the present invention is preferably a bicyclic depsipeptide having the formula (1) wherein B is a cysteine residue; J is a residue of an amino acid selected from the group consisting of leucine, alanine, β-t-butylalanine, valine and phenylalanine; D is a residue of an amino acid selected from the group consisting of valine and alanine; E is a residue of an amino acid selected from the group consisting of leucine, isoleucine, alanine, β-t-butylalanine, valine and phenylalanine; F is a cysteine residue; W is a residue of an amino acid selected from the group consisting of aspartic acid and glutamic acid; Z is a residue of an amino acid selected from the group consisting of aspartic acid, glutamic acid, glutamine and asparagine; G is a disulfide linkage; l, m and n are 0 or 1; p is 0; q is 1; and R is a straight or branched alkyl or alkoxymethyl group of 6–12 carbon atoms, or a pharmacologically acceptable salt thereof.

Other type of the present compound is preferably a bicyclic depsipeptide having the formula (1) wherein A is a residue of an amino acid selected from the group consisting of isoleucine, leucine, alanine, β-t-butylalanine, valine and phenylalanine; B is a cysteine residue; D is a residue of an amino acid selected from the group consisting of valine and alanine; E is a residue of an amino acid selected from the group consisting of leucine, isoleucine, alanine, β-t-butylalanine, valine and phenylalanine; F is a cysteine residue; W is a residue of an amino acid selected from the group consisting of aspartic acid and glutamic acid; Z is a residue of an amino acid selected from the group consisting of aspartic acid, glutamic acid, glutamine and asparagine; G is a disulfide linkage; l, m and n are 0 or 1; p is 1; q is 0; and R is a straight or branched alkyl or alkoxymethyl group of 6–12 carbon atoms, or a pharmacologically acceptable salt thereof.

In the formula (1), preferably n=1 and p+q=1.

Further the present invention relates to a pharmaceutical composition which contains as an active ingredient a therapeutically effective amount of the bicyclic depsipeptide of the formula (1) and a pharmaceutically acceptable carrier therefor.

The invention especially relates to a pharmaceutical composition for promoting the production of apoprotein E which contains as an active ingredient a therapeutically effective amount of the bicyclic depsipeptide of the formula (1) and a pharmaceutically acceptable carrier therefor.

The invention further relates to a pharmaceutical composition for treating neurologic damages, dementia or hyperlipemia which contains as an active ingredient a therapeutically effective amount of the bicyclic depsipeptide of the formula (1) and a pharmaceutically acceptable carrier therefor.

Further the invention relates to a method for treating neurologic damages, dementia or hyperlipemia which comprises administering a therapeutically effective amount of the bicyclic depsipeptide of the formula (1) to a host affected with neurologic damages, dementia or hyperlipemia.

The invention still further relates to use of the bicyclic depsipeptide of the formula (1) for treating neurologic damages, dementia or hyperlipemia.

The above amino acids composing the bicyclic depsipeptide having the formula (1) may be in the form of either L-isomer or D-isomer, while the amino acids represented by A, D, J, W and Z may be preferably L-isomers and the amino acids represented by B and E may be preferably D-isomers.

As preferable examples of the bicyclic depsipeptides represented by the above formula (1) according to this invention, there may be mentioned those compounds wherein R is a straight alkyl or alkoxymethyl group of 6–12 carbon atoms, l, m, n, p and q are 0 or 1 with a proviso that p+q is 1, and B=Cys, J=Leu, W=Asp, D=Ala, E=Leu, F=Cys, Z=Gln and G=S—S;

B=Cys, J=Ala, W=Asp, D=Val, E=Leu, F=Cys, Z=Gln and G=S—S;

B=Cys, J=Leu, W=Asp, D=Val, E=Ile, F=Cys, Z=Gln and G=S—S;

B=Cys, J=Leu, W=Asp, D=Val, E=Ala, F=Cys, Z=Gln and G=S—S;

B=Cys, J=Leu, W=Asp, D=Val, E=Leu, F=Cys, Z=Gln and G=S—S;

A=Ile, B=Cys, W=Asp, D=Ala, E=Leu, F=Cys, Z=Gln and G=S—S;

A=Ile, B=Cys, W=Asp, D=Val, E=Leu, F=Cys, Z=Gln and G=S—S;

A=Ala, B=Cys, W=Asp, D=Val, E=Ile, F=Cys, Z=Gln and G=S—S;

A=Ile, B=Cys, W=Asp, D=Val, E=Ala, F=Cys, Z=Gln and G=S—S;

B=Cys, J=Leu, W=Glu, D=Ala, E=Leu, F=Cys, Z=Gln and G=S—S;

B=Cys, J=Ala, W=Glu, D=Val, E=Leu, F=Cys, Z=Gln and G=S—S;

B=Cys, J=Leu, W=Glu, D=Val, E=Ile, F=Cys, Z=Gln and G=S—S;

B=Cys, J=Leu, W=Glu, D=Val, E=Ala, F=Cys, Z=Gln and G=S—S;

B=Ile, J=Cys, W=Glu, D=Ala, E=Leu, F=Cys, Z=Gln and G=S—S;

A=Ile, B=Cys, W=Glu, D=Val, E=Leu, F=Cys, Z=Gln and G=S—S;

A=Ala, B=Cys, W=Glu, D=Val, E=Ile, F=Cys, Z=Gln and G=S—S;

A=Ile, B=Cys, W=Glu, D=Val, E=Ala, F=Cys, Z=Gln and G=S—S;

B=Ser, J=Leu, W=Asp, D=Ala, E=Leu, F=Glu, Z=Gln and G=O—CO;

B=Ser, J=Ala, W=Asp, D=Val, E=Leu, F=Glu, Z=Gln and G=O—CO;

B=Ser, J=Leu, W=Asp, D=Val, E=Ile, F=Glu, Z=Gln and G=O—CO;

B=Ser, J=Leu, W=Asp, D=Val, E=Ala, F=Glu, Z=Gln and G=O—CO;

B=Ser, J=Leu, W=Asp, D=Val, E=Leu, F=Glu, Z=Gln and G=O—CO;

A=Ile, B=Ser, W=Asp, D=Ala, E=Leu, F=Glu, Z=Gln and G=O—CO;

A=Ile, B=Ser, W=Asp, D=Val, E=Leu, F=Glu, Z=Gln and G=O—CO;

A=Ala, B=Ser, W=Asp, D=Val, E=Ile, F=Glu, Z=Gln and G=O—CO;

A=Ile, B=Ser, W=Asp, D=Val, E=Ala, F=Glu, Z=Gln and G=O—CO;

B=Glu, J=Leu, W=Glu, D=Ala, E=Leu, F=Lys, Z=Gln and G=CONH;

B=Glu, J=Ala, W=Glu, D=Val, E=Leu, F=Lys, Z=Gln and G=CONH;

B=Glu, J=Leu, W=Glu, D=Val, E=Ile, F=Lys, Z=Gln and G=CONH;

B=Glu, J=Leu, W=Glu, D=Val, E=Ala, F=Lys, Z=Gln and G=CONH;

B=Glu, J=Leu, W=Glu, D=Val, E=Leu, F=Lys, Z=Gln and G=CONH;

A=Ile, B=Glu, W=Asp, D=Ala, E=Leu, F=Lys, Z=Gln and G=CONH;

A=Ile, B=Glu, W=Asp, D=Val, E=Leu, F=Lys, Z=Gln and G=CONH;

A=Ala, B=Glu, W=Asp, D=Val, E=Ile, F=Lys, Z=Gln and G=CONH;

A=Ile, B=Glu, W=Asp, D=Val, E=Ala, F=Lys, Z=Gln and G=CONH;

A=Ile, B=Lys, W=Glu, D=Ala, E=Leu, F=Glu, Z=Gln and G=NHCO;

A=Ile, B=Lys, W=Glu, D=Val, E=Leu, F=Glu, Z=Gln and G=NHCO;

A=Ala, B=Lys, W=Glu, D=Val, E=Ile, F=Glu, Z=Gln and G=NHCO;

A=Ile, B=Lys, W=Glu, D=Val, E=Ala, F=Glu, Z=Gln and G=NHCO; or

A=Ile, B=Lys, W=Glu, D=Val, E=Leu, F=Glu, Z=Gln and G=NHCO.

In the description of the present compounds as given above and the Examples and others as shown below, the amino acid or amino acid residue composing the peptide is referred to herein by means of the trilateral expression system generally employed for the designation of amino acids.

More specifically, there are applied the following expressions:

Alanine=Ala, valine=Val, leucine=Leu, isoleucine=Ile, serine=Ser, threonine=Thr, aspartic acid=Asp, asparagine=Asn, glutamic acid=Glu, glutamine=Gln, lysine=Lys, cysteine=Cys, etc.

The bicyclic depsipeptides of the invention may be prepared, for example, by an intramolecular crosslinking of a cyclic depsipeptide prepared according to a conventional peptide synthesis with a disulfide bond, an amide bond or an ester bond as described below:

More specifically, the bicyclic depsipeptide represented by the above formula (1) wherein p is 0 and q is 1 may be prepared by the sequential steps of:

condensing a 3-hydroxypropionic acid derivative represented by the formula (3)

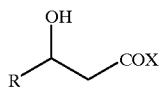
(3)

(wherein X is a protecting group for carboxy group and R is as defined above), which is obtained by protecting the carboxy group of a 3-hydroxypropionic acid derivative represented by the formula (2)

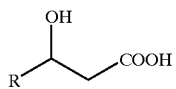
(2)

(wherein R is as defined above) with a suitable protecting group, with an amino acid Y—B'—OH to form a compound represented by the formula (4)

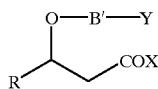
(4)

(wherein Y is an α-amino-protecting group, B' is an amino acid residue corresponding to B wherein the amino group, carboxy group, hydroxy group or mercapto group in the side chain of B are protected, and X and R are as defined above), leaving the amino-protecting group Y in the amino acid B' of the compound thus obtained to form a compound represented by the formula (5)

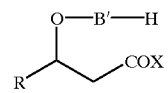
(5)

(wherein B', X and R are as defined above), condensing the compound thus obtained with an amino acid Y—J—OH having a protected α-amino group to form a depsipeptide represented by the formula (6)

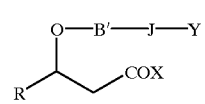
(6)

(wherein B', J, X, Y and R are as defined above), leaving the protecting group Y for amino group of the depsipeptide to form a depsipeptide represented by the formula (7)

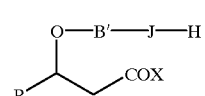
(7)

(wherein B', J, X and R are as defined above), condensing the depsipeptide thus obtained with aspartic acid having a protected amino group and a protected carboxy group at the β-position or glutamic acid having a protected amino group and a protected carboxy group at the γ-position to form a depsipeptide represented by the formula (8)

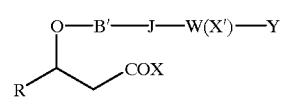
(8)

(wherein X' is a protecting group for a carboxy group at the β-position of aspartic acid or a carboxy group at the γ-position of glutamic acid and B', J, W, X, Y and R are as defined above), leaving the protecting group Y for the amino group of aspartic acid or glutamic acid of the depsipeptide thus obtained to form a depsipeptide represented by the formula (9)

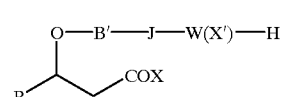
(9)

(wherein B', J, W, X, X' and R are as defined above), condensing the depsipeptide thus obtained with an amino acid Y—D—OH having a protected α-amino group to form a depsipeptide represented by the formula (10)

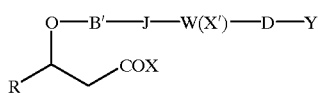
(10)

(wherein B', J, W, D, Y, X, X' and R are as defined above),
leaving the protecting group Y for the amino group of the depsipeptide thus obtained to form a depsipeptide represented by the formula (11)

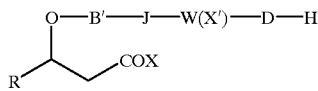
(11)

(wherein B', J, W, D, X, X' and R are as defined above),
condensing the depsipeptide thus obtained with an amino acid Y—E—OH having a protected α-amino group or condensing the depsipeptide of the formula (9) with said amino acid Y—E—OH, without applying the condensation step with said amino acid Y—D—OH, to form a compound represented by the formula (12)

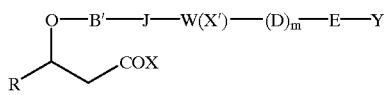
(12)

(wherein B', J, W, D, E, Y, X, X', R are as defined above and m is 0 or 1),
leaving the protecting group Y for the amino group of the depsipeptide thus obtained to form a depsipeptide represented by the formula (13)

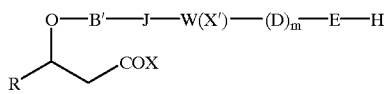
(13)

(wherein B', J, W, D, E, X, X', R and m are as defined above),
condensing the depsipeptide thus obtained with an amino acid Y—F'—OH having a protected amino group at the α-position of the amino acid F and a protected amino group in the side chain or condensing the depsipeptide of the formula (11) or the formula (9) with an amino acid Y—F'—OH having a protected amino group, without applying the condensation step with the amino acid Y—E—OH, to form a depsipeptide represented by the formula (14)

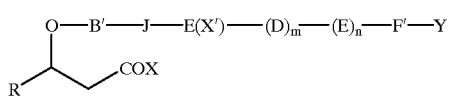
(14)

(wherein B, J, W, D, E, F', Y, X, X', R and m are as defined above),
leaving the protecting group Y for the amino group of the depsipeptide thus obtained to form a depsipeptide represented by the formula (15)

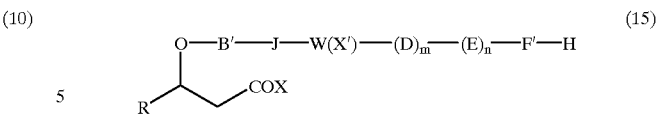
(15)

(wherein B', J, W, D, E, F', X, X', R, m and n are as defined above),
condensing the depsipeptide thus obtained with aspartic acid having a protected amino group and a protected carboxy group at the β-position, asparagine having a protected amino group and a protected carbamido group at the β-position, glutamic acid having a protected amino group and a protected carboxy group at the γ-position or glutamine having a protected amino group and a protected carboxy group at the γ-position to form a depsipeptide represented by the formula (16)

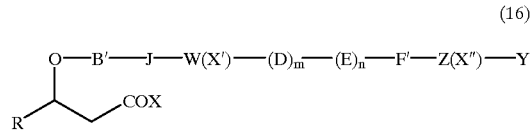
(16)

(wherein X″ is a protecting group for a carboxy group at the β-position of aspartic acid, a carboxy group at the γ-position of glutamic acid, a carbamido group at the β-position of asparagine or a carbamido group at the γ-position of glutamine and B', J, W, D, E, F', Z, X, X', Y, R, m and n are as defined above),
leaving the protecting group X for the carboxy group of the depsipeptide thus obtained to form a depsipeptide represented by the formula (17)

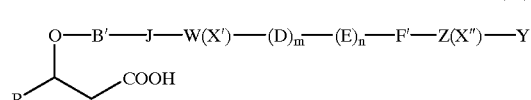
(17)

(wherein B', J, W, D, E, F', Z, Y, X', X″, R, m and n are as defined above),
leaving the protective group for the amino group of aspartic acid, asparagine, glutamic acid or glutamine of the depsipeptide thus obtained, followed by self-condensation to form a cyclic depsipeptide represented by the formula (18)

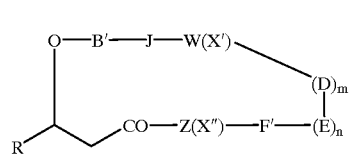
(18)

(wherein B', J, W, D, E, F', Z, X', X″, R, m and n are as defined above),
and in the case of the cyclic depsipeptide wherein B' and F' are cysteine, the step of forming a disulfide bond between two cysteines by using an oxidizing agent such as an acidic iodine solution, or in the case of the cyclic depsipeptide wherein B' is serine and F' is glutamic acid or aspartic acid or wherein B' is glutamic acid or aspartic acid and F' is serine, the step of forming an ester bond by leaving the protecting group for the carboxy and hydroxy groups in the side chain followed by treating with an acidic catalyst or dicyclohexylcarbodiimide or the like, or in the case of the cyclic depsipeptide wherein B' is glutamic acid or aspartic acid and F' is lysine or wherein B' is lysine and F' is glutamic acid or aspartic acid, the step of forming an amido bond by leaving the protecting group for the amino and carboxy groups in the side chain, followed by an amidation reaction with dehydration, whereby a bicyclic depsipeptide may be prepared.

Subsequently, the cyclic depsipeptide obtained as described above may be subjected to removal of the protecting groups for W and Z to prepare a bicyclic depsipeptide represented by the formula (19)

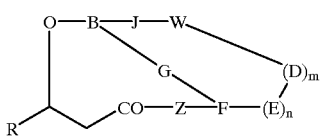

(19)

(wherein B, J, W, D, E, F, Z, R, m and n are as defined above and G is a disulfide bond, an ester bond or an amido bond).

Also, the bicyclic depsipeptide of the formula (20) wherein p is 1 and q is 0

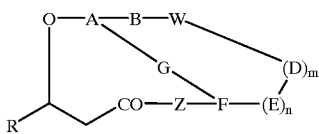

(20)

(wherein A, B, W, D, E, F, Z, G, R, m and n are as defined above) may be prepared according to any of the above synthesis methods.

Also, the bicyclic depsipeptide of the invention may be prepared by self-condensation of a depsipeptide represented by the formula (21), which is prepared according to solid synthesis or the like,

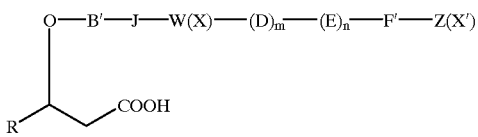

(21)

(wherein B', J, W, D, E, F', Z, X, X', R, m and n are as defined above).

The processes for the preparation of the bicyclic depsipeptide as described above are simply depicted for explaining typical processes solely and there may be made various modifications to the process for the preparation of the depsipeptide. For instance, the cyclic depsipeptide of the formula (18) may be prepared by stepwise condensations of the respective amino acids according to a conventional method for the synthesis of peptides as described above or alternatively by condensation some oligopeptides previously synthesized followed by self-condensation.

For the synthesis steps to obtain the bicyclic depsipeptide of the invention, there may be used any of conventional methods adopted for peptide synthesis.

For instance, there may be mentioned as a process, for forming a peptide linkage, a condensing agent method, an acid anhydride method, an active ester method, a redox method, an enzyme method or the like.

Where peptide synthesis is to be carried out using the condensing agent method, there may be preferably employed N,N-dicyclohexylcarbodiimide (hereinafter referred to as "DCC") or 1-ethyl-3-(3-dimethylaminopropyl)-carbodiimide hydrochloride, i.e. water-soluble carbodiimide (hereinafter referred to as "WSCI"), O-(1H-benzotriazole-1-yl)-N,N,N',N'-tetramethyluronium tetrafluoroborate (hereinafter referred to as "TBTU"), benzotriazole-1-yl-oxy-tris(dimethylamino) phosphonium hexafluorophosphate (hereinafter referred to as "BOP"), O-(7-azabenzotriazole-1-yl)-1,2,3-tetramethyluronium hexafluorophosphate (hereinafter referred to as "HATU") and the like. It is also preferable to simultaneously add an additive commonly employed for preventing racemization such as N-hydroxysuccinimide, N-hydroxy-benzotriazole (hereinafter referred to as "HOBt"), 1-hydroxy-7-azabenzotriazole (hereinafter referred to as "HOAt"), N-hydroxy-5-norbornene-2,3-dicarbodiimide and the like.

As main condensing agents which may be employed in the azide method may be mentioned diphenylphosphoryl azide (hereinafter referred to as "DPPA").

Before carrying out the condensation reaction, it is preferable to apply any protecting procedure to the carboxy group, amino group, ω-carbamido group and the like, which would not participate in said condensation reaction, according to any conventional and well-known procedures.

In this case, as the protecting groups which may be applied in the protecting procedure, there may be mentioned, for example, a t-butoxycarbonyl (hereinafter referred to as "Boc") group, a benzyloxycarbonyl group, a p-methoxy-benzyloxycarbonyl group or a 9-fluorenylmethoxycarbonyl (hereinafter referred to as "Fmoc") or the like as a protecting group for animo group; a benzyloxy group (hereinafter referred to as "OBzl") or a t-butoxy group (hereinafter referred to as "OtBu") or the like as a protective group for carboxyl group; 4,4-dimethoxybenzhydryl (hereinafter referred to as "Mbh") group, a trityl group (hereinafter referred to as "Trt") or the like as a protecting group for terminal carbamido group.

As the protecting group for a hydroxy group, there may be mentioned a OBzl group, a OtBu group, etc.

As the protecting group for a mercapto group, there may be mentioned a benzyl group (hereinafter referred to as "Bn"), a Trt group, an acetamido group (hereinafter referred to as "Acm"), etc.

The leaving reaction of the protecting groups in the preparation steps of the bicyclic depsipeptide of the invention should remove the protecting groups without giving any influence upon the peptide linkages and may be adequately selected depending upon the type of the protecting group as used.

As the solvent which may be employed in each peptide synthesis as explained above, there may be mentioned, for example, anhydrous or hydrous chloroform, dichloromethane, ethyl acetate, N,N-dimethylformamide (hereinafter referred to as "DMF"), dimethyl sulfoxide, pyridine, dioxane, tetrahydrofuran (hereinafter referred to as "THF"), dimethoxyethane, acetonitrile and the like and they may be used in combination with two or more thereof if necessary. The condensation reaction may be carried out in a temperature range of from about −20 to 50° C. according to conventional methods.

Peptide synthesis may be carried out according to any of a liquid phase method and a solid phase method, while a column method or a batch method may be also applicable.

The bicyclic depsipeptides of the invention may be converted to pharmacologically acceptable salts thereof such as metal salts, e.g. sodium, potassium or calcium salt, ammonium salts or organic amine salts, e.g. triethylamine salts, and these pharmacologically acceptable salts may be also used as a promoting agent for the production of apolipoprotein E.

As the 3-hydroxypropionic acid derivative of the formula (2) which is a starting material to be used for the bicyclic depsipeptide represented by the formula (1), there may be illustratively mentioned 3-hydroxy-capric acid, 3-hydroxy-lauric acid, 3-hydroxy-myristic acid and the like.

The 3-hydroxypropionic acid derivative may be in the form of any of D-isomer, L-isomer and racemate.

The bicyclic depsipeptides of the invention may strongly promote the production of apolipoprotein E in Hep G2 cell which is the apolipoprotein-producing cell and then are useful as a therapeutic agent for neurologic damages and also as an antidementia agent. Moreover, they are useful for the treatment of disorders of the peripheral nervous system such as diabetic neuropathy, disorders of the peripheral nervous system caused by deficiency of Vitamin B group ($B_1$, $B_2$, $B_{12}$, etc.) and the like.

The bicyclic depsipeptides or pharmacologically acceptable salts thereof according to the invention may potently promote the production of apolipoprotein E and they are useful as an antihyperlipemic agent.

The bicyclic depsipeptides or pharmacologically acceptable salts thereof according to the invention may be formulated to pharmaceutical preparations of various dosage forms. More specifically, such pharmaceutical preparations may be, for example, solid preparations such as tablets, hard capsules, soft capsules, granules, powders, etc. and liquid preparations such as solutions, emulsions, suspensions, etc. As the preparation for parenteral administration may be mentioned injections, suppositories, etc.

In preparing such pharmaceutical preparations, conventional additives may be incorporated, for example, excipients, stabilizers, antiseptics, solubilizing agents, wetting agents, emulsifying agents, lubricants, sweetening agents, coloring agents, corringents, isotonic agents, buffering agents, antioxidants and the like.

As the additives, there may be mentioned, for example, starch, sucrose, fructose, lactose, glucose, mannitol, sorbitol, precipitated calcium carbonate, crystalline cellulose, carboxymethylcellulose, dextrin, gelatin, acacia gum, magnesium stearate, talc, hydroxypropylmethylcellulose and the like.

Where the bicyclic depsipeptide of the invention is to be applied in the form of solutions or injections, the active ingredient, the bicyclic depsipeptide or pharmacologically acceptable salt thereof, may be used by dissolving or suspending in any conventional diluent. The diluent may include, for example, physiological saline, Ringer's solution, aqueous glucose solution, an alcohol, a fatty acid ester, glycerol, oil and fat derived from plant or animal sources, a paraffin and the like. These preparations may be prepared according to a conventional method.

A usual clinical dose may be in the range; of 0.5–5000 mg per day for adult when orally given. More preferably, it is in the range of 5–500mg.

A usual dose may be in the range of 0.05–5000 mg per day for adult when parenterally administered.

The production of the bicyclic depsipeptide of the invention will be explained below by way of Synthesis Examples, the effect of the promoting action on apolipoprotein E production by the bicyclic depsipeptide of the invention will be done by way of Test Examples and the pharmaceutical preparation comprising as an active ingredient the bicyclic depsipeptide of the invention will be done by way of Preparation Examples.

In the following Examples, in the case where the amino acid composing the depsipeptide and bicyclic depsipeptide is in the form of D-isomer, it shall be specifically indicated to that effect, while unless otherwise indicated the amino acid shall be in the form of L-isomer.

SYNTHESIS EXAMPLE 1

To a solution of a starting alcohol (1.32 g), Fmoc-Cys(Acm) (1.80 g) and DMAP (34 mg) in dichloromethane (25 ml) was added DCC (1.22 g) under ice-cooling. The reaction solution was stirred under ice-cooling for 2 hours and then at room temperature overnight. After the precipitated crystalline substance was filtered off, the solvent was distilled off and ethyl acetate and 10% aqueous citric acid were added. The organic layer obtained by separation was washed successively with water, 10% aqueous sodium hydrogencarbonate and water and then dried over anhydrous sodium sulfate. After the solvent was distilled off, the crude product thus obtained was purified by a silica gel column chromatography to afford 2.88 g of the desired ester.

$^1$H-NMR (δ ppm, $CHCl_3$) 7.76 (d, J=7.3 Hz, 2H), 7.61 (t, J=6.3 Hz, 2H), 7.41 (t, J=7.6 Hz, 2H), 7.27–7.37 (m, 7H), 6.43 (br s, 1H), 5.76 (d, J=5.9 Hz, 1H), 5.27–5.35 (m, 1H), 5.11 (s, 2H), 4.43 (d, J=6.8 Hz, 2H), 4.40–4.53 (m, 1H), 4.35 (d, J=5.9 Hz, 2H), 4.24 (t, J=6.8 Hz, 1H), 3.01–3.10 (m, 1H), 2.86 (dd, J=6.6, 15 Hz, 1H), 2.68 (dd, J=7.6, 16 Hz, 1H), 2.62 (dd, J=4.9, 16 Hz, 1H), 1.97 (s, 3H), 1.51–1.73 (m, 2H), 1.06–1.38 (m, 18H), 0.88 (t, J=6.8 Hz, 3H)

SYNTHESIS EXAMPLE 2

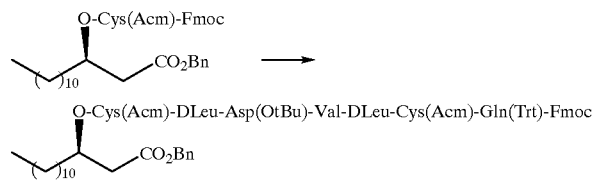

To a solution of the resulting ester (2.85 g) obtained in Synthesis Example 1 in DMF (39 ml) was added diethylamine (3.9 ml). The reaction solution was stirred at room temperature for one hour, the solvent was distilled off and ethyl acetate was added to the residue. The mixture was washed with water and then dried over anhydrous sodium sulfate. After the solvent was distilled off, the crude product thus obtained was purified by a silica gel column chromatography to afford 1.40 g of the amine.

To a solution of the amine (0.53 g) thus obtained (SEQ ID NO: 1), Fmoc-Gln(Trt)-Cys(Acm)-DLeu-Val-Asp(OtBu)-Dleu-OH (1.33 g) (SEQ ID NO: 2) and HOBt (0.14 g) in dichloromethane (25 ml) was added WSCI (0.20 g) under ice-cooling. The reaction mixture was stirred under ice-cooling for 2 hours and then at room temperature overnight. After the solvent was distilled off, chloroform and 10% citric acid were added to the residue. The organic layer obtained by separation was washed successively with water, 5% aqueous sodium hydrogencarbonate and water and then dried over anhydrous sodium sulfate. After the solvent was distilled off, the crude product thus obtained was crystallized from chloroform-ether to afford 1.31 g of the desired ester.

$^1$H-NMR (δ ppm, DMSO-d6) 8.51 (s, 1H), 8.43–8.47 (m, 2H), 8.40 (d, J=7.8 Hz, 1H), 8.26 (d, J=7.3 Hz, 1H), 8.02–8.08 (m, 2H), 7.99 (d, J=8.3 Hz, 1H), 7.87 (d, J=7.8 Hz, 2H), 7.74 (d, J=8.8 Hz, 1H), 7.70 (t, J=6.3 Hz, 2H), 7.51 (d, J=8.3 Hz, 1H), 7.39 (t, J=7.3 Hz, 2H), 7.14–7.36 (m, 22H), 5.07 (s, 2H), 5.02–5.13 (m, 1H), 4.50–4.65 (m, 2H), 4.28–4.47 (m, 4H), 4.09–4.27 (m, 7H), 3.96–4.05 (m, 1H), 2.94 (dd, J=4.9, 14 Hz, 1H), 2.84 (dd, J=4.9, 14 Hz, 1H), 2.77 (dd, J=8.5, 14 Hz, 1H), 2.57–2.71 (m, 4H), 2.25–2.39 (m, 2H), 1.81 (s, 3H), 1.79 (s, 3H), 1.29 (s, 9H), 1.10–1.99 (m, 30H), 0.66–0.88 (m, 21H)

SYNTHESIS EXAMPLE 3

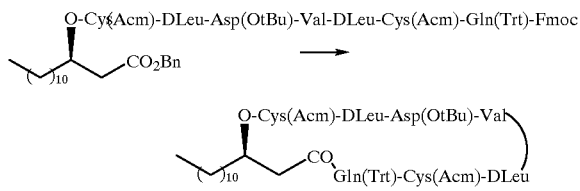

A suspension of the benzyl ester (1.20 g) thus obtained in Synthesis Example 2 (SEQ ID NO: 1) and 10% palladium-carbon (5 g) in methanol-DMF was allowed to react under hydrogen atmosphere at room temperature for one hour. After completion of the reaction, the palladium-carbon was filtered off and the solvent was distilled off.

The carboxylic acid thus obtained (SEQ ID NO: 3) was dissolved in a 20% piperidine solution in DMF (15 ml) and the resulting solution was stirred for 30 minutes. After the solvent was distilled off, the crude product thus obtained was purified by a silica gel column chromatography to afford 0.64 g of an aminocarboxylic acid.

To a solution of the aminocarboxylic acid thus obtained in DMF (600 ml) were added diisopropylethylamine (0.31 ml), HOAt (0.18 g) and HATU (0.50 g) and the mixture was stirred at room temperature overnight. After the solvent was distilled off, ethyl acetate and 5% aqueous potassium hydrogensulfate were added. The organic layer obtained by separation was washed successively with water and saturated aqueous sodium chloride and then dried over anhydrous sodium sulfate. After the solvent was distilled off, the crude product thus obtained was purified by a silica gel column chromatography to afford 0.44 g of the desired compound.

$^1$H-NMR (δ ppm, CDCl$_3$) 8.90 (s, 1H), 8.13 (d, J=8.8 Hz, 1H), 7.99 (t, J=6.3 Hz, 1H), 7.63 (d, J=6.8 Hz, 1H), 7.56 (d, J=8.8 Hz, 1H), 7.13–7.38 (m, 16H), 6.91 (s, 1H), 6.75 (d, J=9.3 Hz, 1H), 6.53 (br s, 1H), 6.08 (br s, 1H), 5.08–5.15 (m, 1H), 4.86–4.96 (m, 1H), 4.55–4.64 (m, 2H), 4.38–4.53 (m, 3H), 3.97–4.18 (m, 4H), 3.84–3.92 (m, 1H), 3.22–3.42 (m, 2H), 3.06–3.18 (m, 2H), 2.52–2.81 (m, 2H), 2.30–2.45 (m, 2H), 1.99 (2s, 6H), 1.10–2.22 (m, 30H), 1.44 (s, 9H), 0.81–1.10 (m, 21H)

SYNTHESIS EXAMPLE 4

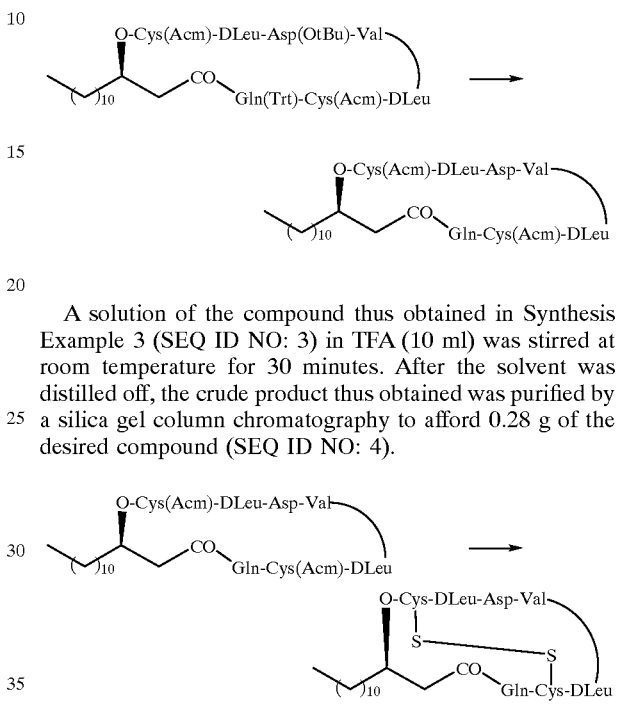

A solution of the compound thus obtained in Synthesis Example 3 (SEQ ID NO: 3) in TFA (10 ml) was stirred at room temperature for 30 minutes. After the solvent was distilled off, the crude product thus obtained was purified by a silica gel column chromatography to afford 0.28 g of the desired compound (SEQ ID NO: 4).

A solution of the compound (50 mg) thus obtained (SEQ ID NO: 4) in 80% methanol (50 ml) was added dropwise under ice-cooling a mixture of methanol (50 ml), 6M hydrochloric acid (20 ml) and an iodine solution (380 mg of iodine dissolved in 75 ml of methanol). The resulting mixture was stirred under ice-cooling for 10 minutes and then an aqueous solution of ascorbic acid (ascorbic acid 400 mg/100 ml) was added dropwise until the coloring of iodine disappeared. After the methanol was distilled off, the residue was extracted twice with a 10% methanolic solution of chloroform. The resulting extract was dried over anhydrous sodium sulfate. After the solvent was distilled off, the crude product thus obtained was crystallized from ether to afford 23 mg of the desired bicyclic depsipeptide (Compound 1) (SEQ ID NO: 5).

MS (M$^+$); 998

$^1$H-NMR (δ ppm, CDCl$_3$) 12.2 (s, 1H), 8.82 (d, J=9.3 Hz, 1H), 8.60 (d, J=6.8 Hz, 1H), 8.48 (d, J=6.8 Hz, 1H), 8.53 (br s, 1H), 8.17 (d, J=4.4 Hz, 1H), 7.92 (d, J=8.8 Hz, 1H), 7.47 (d, J=6.8 Hz, 1H), 7.27 (s, 1H), 6.72 (s, 1H), 5.40 (s, 1H), 5.07 (br s, 1H), 4.90–5.01 (m, 1H), 4.53–4.66 (m, 1H), 3.97–4.51 (m, 4H), 3.51–3.64 (m, 2H), 2.57–3.06 (m, 6H), 1.99–2.18 (m, 3H), 1.69–1.96 (m, 3H), 1.34–1.68 (m, 7H), 1.10–1.22 (m, 18H), 0.67–0.95 (m, 21H)

TEST EXAMPLE 1

It will be shown below that Compound 1 obtained in Synthesis Example 4 has a promoting activity on the production of apolipoprotein E in Hep G2 cells, together with the test procedures as used.

First, Hep G2 cells of 1×10$^5$ cells were suspended in per mol of Dulbecco's modified Eagle medium (manufactured by Nissui Seiyaku Co., Ltd.; hereinafter referred to as "D-MEM medium") containing 10% fetal bovine serum and per ml each of the suspension was poured into a 24-well tissue culture plate. The cells were cultivated at 37° C. under atmosphere of a mixed gas composed of 5% carbon dioxide and 95% air for three days. The medium was removed by means of a pipette, 1 ml of a fresh D-MEM medium was added to the residue and the resulting mixture was again cultivated at 37° C. under atmosphere of a mixed gas composed of 5% carbon dioxide and 95% air for one day. Thereafter, the medium was removed by means of a pipette and washed three times with 0.5 ml of a fresh D-MEM medium. There were added to the resulting cells 1 ml of a fresh D-MEN medium and 10 μl of a methanolic solution of Compound 1, namely, the bicyclic depsipeptide of the invention at the concentration as shown in Table 3. Then, cultivation was continued at 37° C. for 7 hours and the cultured broth was adopted as a sample. The apolipoprotein E produced in the cultured broth was assayed by means of an enzyme immunoassay method.

The compositions of the buffers applied in the enzyme immunoassay are summarized in the following Table 1. In this connection, PBS represents phosphate-buffered saline, PBS-T represents phosphate-buffered saline having incorporated Tween 20 and a blocking solution is the phosphate buffer containing the immunosuppressive agent "Block Ace" which is derived from lactoprotein and manufactured by Dainippon Pharmaceutical Co., Ltd.

TABLE 1

| PBS (pH 7.2) | |
| --- | --- |
| KH$_2$PO$_4$ | 0.2 g |
| Na$_2$HPO$_4$·12H$_2$O | 2.9 g |
| NaCl | 8.0 g |
| KCl | 0.2 g |
| Distilled water | q.s. |
| Total | 1000 ml |
| PBS-T (pH 7.2) | |
| KH$_2$PO$_4$ | 0.2 g |
| Na$_2$HPO$_4$·12H$_2$O | 2.9 g |
| NaCl | 8.0 g |
| KCl | 0.2 g |
| Tween 20 | 0.5 g |
| Distilled water | q.s. |
| Total | 1000 ml |
| Blocking solution (pH 7.2) | |
| Block Ace | 250 ml |
| KH$_2$PO$_4$ | 0.2 g |
| Na$_2$HPO$_4$·12H$_2$O | 2.9 g |
| NaCl | 8.0 g |
| KCl | 0.2 g |
| Distilled water | q.s. |
| Total | 1000 ml |

The mouse antihuman apolipoprotein E monoclonal antibody (manufactured by BYOSIS, S. A., France) was dissolved in a 0.05M aqueous sodium hydrogencarbonate solution (pH 9.5) at a concentration of 5 μg/ml. 50 μl each of this solution was poured into Nunc immunoplates which were then allowed to stand at 4° C. for 16 hours. They were washed three times with 300 μl of PBS, 300 μl of the blocking solution was added and the mixture was allowed to stand at 37° C. for 2 hours.

It was again washed three times with 300 μl of PBS, 50 μl of the above cultured broth was added and the mixture was allowed to stand at room temperature for 2 hours. After washing three times with 300 μl of PBS-T, 50 μl of a 3000-fold diluted solution (10% aqueous Block Ace solution) of goat anti-apolipoprotein E polyclonal antibody (manufactured by Chemicon Co., Ltd., U. S. A.) was added and the mixture was allowed to stand at room temperature for 2 hours. The mixture was washed three times with 300 μl of PBS-T, a 5000-fold diluted solution (a 10% aqueous solution of Block Ace) of a peroxidase-labeled anti-goat TgG polyclonal antibody (manufactured by Bindingsite Co., Ltd., U. K.) was added and the mixture was allowed to stand at 20 room temperature for 2 hours. After washing five times with 300 μl of PBS-T, 100 μl of a coloring solution (Composition: 0.1M potassium citrate (pH 4.5) 1 ml, 30% aqueous hydrogen peroxide 0.4 μl, orthophenylenediamine 1 mg) was added and the mixture was allowed to stand for 2 minutes. The reaction was quenched by adding 100 μl of 2N sulfuric acid and absorbance was measured at 490 nm using absorbance at 650 nm as a control. An absolute amount of apolipoprotein E in the present depsipeptide was determined upon the calibration curve drawn up when a commercially available apolipoprotein E (Chemicon Co., Ltd., U. S. A.) was used as a standard.

In this Test Example, the same procedure as described above was carried out except that methanol alone was added instead of the methanolic solution of the bicyclic depsipeptide of the invention and then an apolipoprotein E amount was measured as a control.

A relative apolipoprotein E amount by the present depsipeptide was represented in terms of a relative value (%) when the amount of the control was defined as 100.

As shown in Table 2, it was proved that the Compound 1 of the invention has a potent promoting activity of the production of apolipoprotein E at 1 or 5 μM.

TABLE 2

| Compound | Conc. (μM) | Relative amount of apolipoprotein E (%) |
| --- | --- | --- |
| 1 | 1 | 196 |
|   | 5 | 230 |

From the above test results, it is proved that the bicyclic depsipeptides of the invention can potently promote the production of apolipoprotein E by Hep G2 cells, and therefore, they are useful as a novel type of a therapeutic agent for neurologic damages, an antidementia agent and an antihyperlipemic agent.

Preparation Examples

| Preparation Example 1: Tablets (per tablet) | |
| --- | --- |
| Compound 1 | 20 mg |
| Magnesium silicate | 20 mg |
| Lactose | 98.5 mg |
| Hydroxypropylcellulose | 7.5 mg |
| Magnesium stearate | 1 mg |
| Hydrogenated vegetable oil | 3 mg |
| Total | 150 mg |

Compound 1, magnesium silicate and lactose were admixed and kneaded with an alcoholic solution of hydroxypropylcellulose and then granulated to appropriate particle size, dried, and sized. Then, magnesium stearate and hydrogenated vegetable oil were added and blended to form uniform granules. The granules were then prepared to tablets, each having a diameter of 7.0 mm, a weight of 150 mg and a hardness of 6 kg, by means of a rotary tableting machine.

Preparation Example 2: Granules

| | |
|---|---|
| Compound 1 | 10 mg |
| Magnesium oxide | 40 mg |
| Dibasic calcium phosphate | 38 mg |
| Lactose | 10 mg |
| Hydroxypropylcellulose | 20 mg |

All materials of the above formulation except for hydroxypropylcellulose were uniformly admixed, kneaded with an alcoholic solution of hydroxypropylcellulose and then granulated by means of an extrusion granulation machine and dried to form granules. The granules were sized so as to pass through a 12 mesh sieve and remain on a 48 mesh sieve, whereby granules were prepared.

Preparation Example 3

Syrups

| | |
|---|---|
| Compound 1 | 1.000 g |
| Sucrose | 30.000 g |
| D-Sorbitol 70 w/v % | 25.000 g |
| Ethyl paraoxybenzoate | 0.030 g |
| Propyl paraoxybenzoate | 0.015 g |
| Flavoring agent | 0.200 g |
| Glycerol | 0.150 g |
| 96% Ethanol | 0.500 g |
| Purified water | q.s. |
| Total | 100 ml |

Sucrose, D-sorbitol, ethyl paraoxybenzoate, propyl paraoxybenzoate and Compound 1 were dissolved in purified water (warm water). After cooling, a solution of flavoring agent in glycerol and ethanol was added and then to the mixture was added purified water to make up a volume to 100 ml.

Preparation Example 4: Injections

| | |
|---|---|
| Sodium salt of Compound 1 | 10.0 mg |
| Sodium chloride | 81.0 mg |
| Sodium hydrogencarbonate | 8.40 mg |
| Distilled water for injection | q.s. |
| Total | 10.0 ml |

Sodium hydrogencarbonate, sodium chloride and sodium salt of Compound 1 were dissolved in distilled water to make up a total amount to 10.0 ml.

Preparation Example 5

Suppositories

| | |
|---|---|
| Compound 1 | 2 g |
| Macrogol 4000 | 20 g |
| Glycerol | 78 g |
| Total | 100 g |

Compound 1 was dissolved in glycerol and then Macrogol 4000 was added and dissolved by warming. Then, the mixture was injected into a suppository die and solidified by cooling to prepare suppositories, each weighing 1.5 g.

The bicyclic depsipeptides of the invention have a promoting activity on the production of apolipoprotein E. Since apolipoprotein E has a repairing activity on neurologic damages, the present depsipeptides are useful as a therapeutic agent for neurologic damages, especially as an antidementia agent. Moreover, since apolipoprotein E has an activity of lowering cholesterol and triglyceride levels in blood, the present depsipeptides are useful as an antihyperlipemic agent.

What is claimed is:

1. A bicyclic depsipeptide having the formula (1)

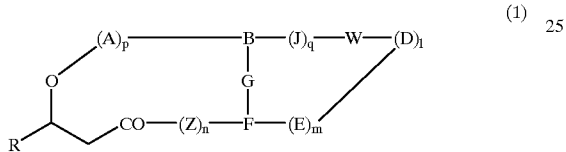

wherein:

R is a straight or branched alkyl group of 5–20 carbon atoms or a straight or branched alkoxymethyl group of 5–15 carbon atoms; A, D, E and J independently are a residue of an amino acid selected from the group of alanine, valine, leucine, isoleucine, serine, threonine, lysine, hydroxylysine, arginine, cysteine, methionine, phenylalamine, tyrosine, tryptophan, histidine, proline, 4-hydroxyproline, aspartic acid, glutamic acid, piperidine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)piperidylalanine, 3-(2-naphthyl)alanine, β-cyclohexylalanine, β-t-butylalanine, 9-anthracenylalanine, α-methylalanine or a (C$_1$–C$_4$) alkyl substituted amino acid residue of said amino acid;
B and F are the same or different and a residue of an amino acid selected from the group consisting of cysteine, aspartic acid, glutamic acid, lysine, hydroxylysine and serine; G is a disulfide bond, an amido bond or an ester bond; W is a residue of an amino acid selected from the group consisting of aspartic acid and glutamic acid; Z is a residue of an amino acid selected from the group consisting of aspartic acid, asparagine, glutamic acid and glutamine; l, m, n, p and q independently are 0 or 1; provided that G is formed by binding each other a thiol, carboxy, hydroxyl or amino group contained in the amino acid residues B and F, a free amino, carboxyl, hydroxyl, mercapto or ω-carbamido group which possibly exists in said amino acid residue may be protected by a group commonly used in peptide chemistry as a protective group and when A, B, D, E, F, J, W and Z are a residue of lysine, hydroxylysine, glutamic acid or aspartic acid, either α- or ω-amino or carboxyl group existing in said residue may form a peptide linkage with its adjacent amino acid, or a and an acceptable carrier thereof.

2. The bicyclic depsipeptide of the formula (1) as claimed in claim 1 wherein A, J, D and E independently are a residue of an amino acid selected from the group consisting of alanine, valine, leucine, isoleucine, serine, threonine, lysine, arginine, cysteine, methionine, phenylalanine, tyrosine, tryptophan, histidine, proline, aspartic acid and glutamic acid or an N-(C$_1$–C$_4$) alkyl substituted amino acid residue of said amino acid, or a and an acceptable carrier thereof.

3. The bicyclic depsipeptide of the formula (1) as claimed in claim 1 or 2 wherein B is a cysteine residue; J is a residue of an amino acid selected from the group consisting of leucine, alanine, β-t-butylalanine, valine and phenylalanine; D is a residue of an amino acid selected from the group consisting of valine and alanine; E is a residue of an amino acid selected from the group consisting of leucine, isoleucine, alanine, β-t-butylalanine, valine and phenylalanine; F is a cysteine residue; W is a residue of an amino acid selected from the group consisting of aspartic acid and glutamic acid; Z is a residue of an amino acid selected from the group consisting of aspartic acid, glutamic acid, glutamine and asparagine; G is a disulfide linkage; l, m and n are 0 or 1; p is 0; and q is 1; and R is a straight or branched alkyl or alkoxymethyl group of 6–12 carbon atoms, or a and an acceptable carrier thereof.

4. The bicyclic depsipeptide of the formula (1) as claimed in claim 1 or 2 wherein A is a residue of an amino acid selected from the group consisting of isoleucine, leucine, alanine, β-t-butylalanine, valine and phenylalanine; B is a cysteine residue; D is a residue of an amino acid selected from the group consisting of valine and alanine; E is a residue of an amino acid selected from the group consisting of leucine, isoleucine, alanine, β-t-butylalanine, valine and phenylalanine; F is a cysteine residue; W is a residue of an amino acid selected from the group consisting of aspartic acid and glutamic acid; Z is a residue of an amino acid selected from the group consisting of aspartic acid, glutamic acid, glutamine and asparagine; G is a disulfide linkage; l, m and n are 0 or 1; p is 1; and q is 0; and R is a straight or branched alkyl or alkoxymethyl group of 6–12 carbon atoms, and an acceptable carrier thereof.

5. A pharmaceutical composition which comprises as an active ingredient the bicyclic depsipeptide as claimed in claim 1 and an acceptable carrier therefor.

6. A pharmaceutical composition for promoting the production of apolipoprotein E which comprises as an active ingredient the bicyclic depsipeptide as claimed in claim 1 and an acceptable carrier therefor.

7. The bicyclic depsipeptide of claim 1, wherein said depsipeptide has the formula (SEQ ID NO:5):

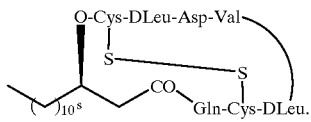

8. A composition which comprises as an active ingredient the bicyclic depsipeptide as claimed in claim 7 and an acceptable carrier therefor.

9. A composition for promoting the production of apolypoprotein E which comprises as an active ingredient the bicyclic depsipeptide as claimed in claim 7 and an acceptable carrier therefor.

* * * * *

UNITED STATES PATENT AND TRADEMARK OFFICE
CERTIFICATE OF CORRECTION

PATENT NO. : 6,211,145 B1
DATED : April 3, 2001
INVENTOR(S) : Makoto Yanai et al.

It is certified that error appears in the above-identified patent and that said Letters Patent is hereby corrected as shown below:

Column 22,
Line 25, "acid, or a and" should read -- acid, and --;
Line 36, "acid, or a and" should read -- acid, and --;
Line 54, "atoms, or a and" should read -- atoms, and --.

Column 23,
Line 10, "carrier therefor." should read -- carrier thereof. --;
Line 14, "carrier therefor." should read -- carrier thereof. --.

Column 24,
Line 10, "carrier therefor." should read -- carrier thereof. --;
Line 14, "carrier therefor." should read -- carrier thereof. --.

Signed and Sealed this

Eighth Day of January, 2002

Attest:

JAMES E. ROGAN
*Attesting Officer*   *Director of the United States Patent and Trademark Office*

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:depsipeptide
<220> FEATURE:
<223> OTHER INFORMATION: X at position 1 is a modified Cys
<220> FEATURE:
<223> OTHER INFORMATION: X at position 2 is DLeu
<220> FEATURE:
<223> OTHER INFORMATION: X at position 3 is Asp(OtBu)
<220> FEATURE:
<223> OTHER INFORMATION: X at position 5 is DLeu
<220> FEATURE:
<223> OTHER INFORMATION: X at position 6 is Cys(Acm)
<220> FEATURE:
<223> OTHER INFORMATION: X at position 7 is Glu(Trt)-Fmoc
```

<400> SEQUENCE: 1

Xaa Xaa Xaa Val Xaa Xaa Xaa
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:depsipeptide
<220> FEATURE:
<223> OTHER INFORMATION: X at position 1 is Fmoc-Gln(Trt)
<220> FEATURE:
<223> OTHER INFORMATION: X at position 2 is Cys(Acm)
<220> FEATURE:
<223> OTHER INFORMATION: X at position 3 is DLeu
<220> FEATURE:
<223> OTHER INFORMATION: X at position 5 is Asp(OtBu)
<220> FEATURE:
<223> OTHER INFORMATION: X at position 6 is DLeu-OH

<400> SEQUENCE: 2

Xaa Xaa Xaa Val Xaa Xaa
 1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:depsipeptide
<220> FEATURE:
<223> OTHER INFORMATION: X at position 1 is a modified Cys(Acm)
<220> FEATURE:
<223> OTHER INFORMATION: X at position 2 is DLeu
<220> FEATURE:
<223> OTHER INFORMATION: X at position 3 is Asp(OtBu)
<220> FEATURE:
<223> OTHER INFORMATION: X at position 5 is DLeu
<220> FEATURE:
<223> OTHER INFORMATION: X at position 6 is Cys(Acm)
<220> FEATURE:
<223> OTHER INFORMATION: X at position 7 is modified Gln(Trt)

<400> SEQUENCE: 3

Xaa Xaa Xaa Val Xaa Xaa Xaa
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:depsipeptide
<220> FEATURE:
<223> OTHER INFORMATION: X at position 1 is modified Cys(Acm)
<220> FEATURE:
<223> OTHER INFORMATION: X at position 2 is DLeu
<220> FEATURE:
<223> OTHER INFORMATION: X at position 5 is DLeu
<220> FEATURE:
<223> OTHER INFORMATION: X at position 6 is Cys(Acm)
<220> FEATURE:
<223> OTHER INFORMATION: X at position 7 is modified Gln

<400> SEQUENCE: 4

Xaa Xaa Asp Val Xaa Xaa Xaa
 1               5

<210> SEQ ID NO 5
<211> LENGTH: 7

```
<212> TYPE: PRT
<213> ORGANISM: Artificial Sequence
<220> FEATURE:
<223> OTHER INFORMATION: Description of Artificial Sequence:depsipeptide
<220> FEATURE:
<223> OTHER INFORMATION: X at position 1 is modified Cys
<220> FEATURE:
<223> OTHER INFORMATION: X at position 2 is DLeu
<220> FEATURE:
<223> OTHER INFORMATION: X at position 5 is DLeu
<220> FEATURE:
<223> OTHER INFORMATION: X at position 6 is modified Cys
<220> FEATURE:
<223> OTHER INFORMATION: X at position 7 is modified Gln

<400> SEQUENCE: 5

Xaa Xaa Asp Val Xaa Xaa Xaa
 1               5
```